United States Patent [19]

Krüger et al.

[11] Patent Number: 5,154,931
[45] Date of Patent: Oct. 13, 1992

[54] GROWTH-STIMULATING MATERIAL DERIVED FROM PORCINE BONE THEREFOR AND A MANUFACTURING PROCESS

[75] Inventors: Wolfgang Krüger, Göttingen; Hubert Mayer, Wolfenbüttel; Karl G. Kukoschke, Braunschweig; Klaus D. Schlüter, Braunschweig; Günter Delling, Braunschweig, all of Fed. Rep. of Germany

[73] Assignee: Gesellschaft fur Biotechnologische Forschung mbH (GBF), Braunschweig, Fed. Rep. of Germany

[21] Appl. No.: 228,923
[22] PCT Filed: Oct. 20, 1987
[86] PCT No.: PCT/EP87/00617
§ 371 Date: Aug. 12, 1988
§ 102(e) Date: Aug. 12, 1988

[30] Foreign Application Priority Data

Oct. 22, 1986 [DE] Fed. Rep. of Germany ....... 3635945
Dec. 22, 1986 [DE] Fed. Rep. of Germany ....... 3643989

[51] Int. Cl.$^5$ ............................................. A61K 35/32
[52] U.S. Cl. .................................... 424/549; 530/840
[58] Field of Search .................. 424/520, 549, 572; 530/840

[56] References Cited

U.S. PATENT DOCUMENTS 4,434,094 2/1984 Seyedin et al. ..................... 530/840
4,627,982 12/1986 Seyedin et al. ..................... 424/549
4,804,744 2/1989 Sen ..................................... 424/549

FOREIGN PATENT DOCUMENTS 0148155 7/1985 European Pat. Off. .

OTHER PUBLICATIONS

Urist et al. BA78:730 1984.

Primary Examiner—Douglas W. Robinson
Assistant Examiner—Jean C. Witz
Attorney, Agent, or Firm—Kane, Dalsimer, Sullivan, Kurucz, Levy, Eisele and Richard

[57] ABSTRACT

The invention relates to a therapeutic composition (especially for bone lesions with cavity formation and parodontitis) containing a growth-stimulating material and a solid carrier, to such a material and to a process for the preparation thereof.

11 Claims, No Drawings

GROWTH-STIMULATING MATERIAL DERIVED FROM PORCINE BONE THEREFOR AND A MANUFACTURING PROCESS

BACKGROUND OF THE INVENTION

1. Field of the Invention

The invention relates to a therapeutic composition for use in parodontal treatment.

According to the findings of the WHO, inflammatory diseases of the teeth-holding system (parodontitis, often also called "parodontosis") are amongst the most widely distributed chronic diseases The long-term preservation of teeth is endangered by the disintegration of the jaw bone occurring in these diseases (especially in the form of deep bone cavities).

Although the previously propagandized rather radical methods involving recontouring of the bone and the soft tissue provided a result that could readily be checked, at the same time parodontal regeneration was not attempted and occasionally even the loss of healthy parodontal tissue was caused;

2. Brief Description of the Prior Art

The aim of modern parodontal treatment is the regeneration of parodontal tissue by cleaning the roots of teeth to remove microbial plaque (concrements), and to remove from the bone cavities tissue modified by inflammation. Numerous methods of treatment of parodontal lesions have been developed for this; cf., inter alia, Prichard 1975, Rosling et al. 1976, Polson et al. 1978, Ramfjord & Ash 1979 and Rateitschak et al. 1984. A certain parodontal regeneration should occur either by merely cleaning the osseous lesions, or by implanting various materials into the bone cavities; The implantation material preferably used today is hydroxyapatite which, according to clinical tests, appears to bring about a greater repair of the lesion than simple root and lesion cleaning;

In all of the cases mentioned, however, there is one fundamental problem. Daughter cells growing out from the oral epithelium form along the surface of the root a new epithelium, which in most cases covers the whole of the treated surface of the root and later may even lie at the apex of the regenerated bone. This epithelium may promote a new inflammation in the depths of the treated bone lesion. The basic problem, however, is that the deep growth of the epithelium proceeds more quickly than does the osseous and desmodontal regeneration.

In order to prevent this deep growth of the epithelium, according to more recent research the bone lesion was covered, for example, with millipore filter before the mucoperiosteal flap was put back in position. This is intended to render possible parodontal regeneration without interference from deep growth of the epithelium. This process appears very complicated, however, and the prognosis is uncertain as a result of a high quota of possible errors.

SUMMARY OF THE INVENTION

One aim of the invention is to provide a therapeutic composition with which the regeneration time is reduced and the risk of deep growth of the epithelium is prevented.

This object is achieved in accordance with the invention by a therapeutic composition having a growth-stimulating material and a solid carrier.

The person skilled in the art is familiar with growth-stimulating materials; attention is drawn to the prior art, which is referred to in the following in connection with a growth-stimulating material according to the invention that is especially suitable.

Growth-stimulating materials are available in liquid or paste form, their growth-stimulating action being attributable to proteins. The purpose of the carrier provided in accordance with the invention is to bind the growth-stimulating material so as to prevent it from being washed away from the site of application.

Examples of carriers that can be used in accordance with the invention are partially to fully absorbable carriers, especially hydroxyapatite (HAP), tricalcium phosphate, collagen and plastics. As a result of the absorbability of the carrier, the therapeutic composition according to the invention can disappear at the site of application, whilst the bone is built up again by the action of the growth-stimulating material.

Growth-promoting activities of bone material have been described by various research groups; see Simpson E. (1984) TIBS 9, pp. 527–530 and Canalis E. (1983) Endocrine Reviews 4, pp. 62–77.

The research group Baylink et al. isolated from human material a growth-promoting substance having a high molecular weight of 83 kD (hSGF=human Skeletal Growth Factor), which promoted the growth of osteoblast-analogous cells from hen embryos with a high content of alkalne phosphatase; see Farley et al. (1982) Biochemistry 21, pp. 3502–3507 and Farley et al. (1982) Biochemistry 21, pp. 3508–3517. At the same time, the dry weight of embryonic hen bones in organ culture was increased in comparison with untreated control cultures by the addition of hSGF. In a later publication, the target cells, which react positively to this growth-promoting substance or human factor, were comprehensively described. Apart from the osteoblast-analogous cells already mentioned, skin and cartilage cells of embryonic hens, human bone cells and skin cells, human osteosarcoma cells and Balb/3T3 cells were also described as being positively stimulable; see Mohan et al (1984) Calcif. Tissue Int. 36, pp. 139–145.

Furthermore, there has also been described; see Jennings et al. (1985) Proc. Fed. Am. Soc. Exp. Biol. 44, p. 1099, No. 4025 the isolation from bone material of cows of a growth-promoting substance (bSGF=bovine Skeletal Growth Factor) having a molecular weight, after reduction with $\beta$-mercaptoethanol, in the range of from 11 to 12 kD. The Urist et al. research group isolated from bovine bone a protein having a molecular weight of 18.5±0.5 kD that induces bone formation in living animals. This growth-promoting substance (bBMP=bovine Bone Morphogenetic Protein) was administered into muscle material of living mice; see Urist et al. (1984) PNAS 81, pp. 371–375 where it induced bone formation; also, bone lesions of cranial bone in dogs were treated by the administration of bBMP.

A similar growth-promoting substance (hBMP=human Bone Morphogenetic Protein) having a molecular weight of 17.5 kD was isolated from human bone material by the same research group; see Klausner A (1985) Biotechnology 3, pp, 507–511.

The Seyedin et al. research group; see Seyedin et al. (1985) PNAS 82, pp. 2267–2271 isolated two proteins from bovine bone which induced in vitro the formation of cartilage cells from cells of mesodermal origin (CIF-A and CIF-B=Cartilage Inducing Factor A and B). The molecular weight of CIF-A and CIF-B was quoted in each case as 26 kD under non-reducing conditions.

The isolation from bone material of rats of a growth-promoting substance (rSGF=rat Skeletal Growth Factor) having a molecular weight of from 6 to 17.5 kD has also been described. The research group of Canalis et al. isolated from an in vitro culture medium of foetal rat cranial bone two proteins (BDGF-1 and BDGF-2) which stimulated the growth of cells of mesodermal origin in organ culture; see Canalis et al. (1980) Science 210, pp. 1021-1023. The molecular weights of these proteins from the culture medium were quoted as 10 kD for BDGF-1 and from 25 to 30 kD for BDGF-2. Only BDGF-2 possessed a mitogenic action.

Growth stimulation of cells

The factor from human tissue isolated by Baylink et al. (hSGF) effects especially a stimulation in the growth of calvaria cells that have a high content of alkaline phosphatase Farley et al., supra.

The activity of bBMP was not tested in monolayer cultures; Urist et al., supra. and Klausner supra. CIF-A and CIF-B cause an increase in the growth of chondrocytes, but this increase in growth was not tested in monolayer cultures Seyedin et al., supra.

The target cells for BDGF-2 were not described in detail; Mohan et al., supra and Canalis et al., supra.

Growth stimulation of bone hSGF causes an increase in the dry weight of embryonic tubular bone in organ culture; see Farley et al., supra, but which types of cell at which parts of these organ cultures have been promoted in their growth was not indicated for hGSF.

No results that relate to in vitro organ cultures of embryonic tubular bone have been published for bBMP, CIF-A, CIF-B and BDGF-2.

Temperature estability of growth stimulation hSGF is described as stable in a temperature range of from 55° to 75°C.[3], the investigations concerning this property having been carried out on osteoblast-analogous cells see Farley et al., supra.

There is no data available on bBMP concerning this property. CIF-A and CIF-B, on the other hand, are stable for 3 minutes at 100° C.

Heat stability is mentioned for BDGF-2, Mohan et al., supra but no values are given.

pH stability hSGF is stable in a pH range of from 2.5 to 10, but no target cells on which these properties were tested were given see Farley et al., supra.

There are no published tests on the acid stability of bBMP, CIF-A and CIF-B.

BDGF-2 is acid-stable, see Mohan et al., supra, but no data on the pH range or the target cells were published.

Molecular weight range hSGF appears to exist in two forms. A high molecular weight form of hSGF exists in 25 mM phosphate buffer (pH 7.2) see Farley et al., supra. On the other hand, after treatment with 4M guanidinium hydrochloride, reversed phase high pressure liquid chromatography and reduction, bSGF is indicated as having a molecular weight of from 11 to 12 kD Jennings et al. supra. There are no details for hSGF and bSGF regarding the use of gel filtration columns with 4M guanidinium hydrochloride as eluant.

CIF-A and CIF-B have an apparent molecular weight of 26 kD each according to gel electrophoresis see Seyedin et al., supra.

There are similarly no details on the molecular weight of BDGF-2 using gel filtration columns with 4M guanidinium hydrochloride as eluant.

Behaviour on copper (II) sulphate-chelate columns

There are no details on the behaviour of hSGF, bSGF, bBMP, CIF-A, CIF-B and BDGF-2 on copper-(II) sulphate-chelate columns.

Behaviour on reversed phase columns bSGF can be bound to reversed phase columns (Reversed Phase HPLC) but can be eluted again with an acetonitrile gradient; see Jennings et al., supra, there are no details on the range of concentration. bBMP, CIF-A and CIF-B can also be bound to a reversed phase column and eluted with an acetonitrile gradient; see Urist el al., supra. and Seyedin et al., supra.

There are no details on the binding capacity of BDGF-2 to reversed phase columns.

Extraction

Various extraction processes have been described for the mentioned State of the Art growth-promoting substances.

Ends of human femorae have been used as the bone material for isolating hSGF; Farley et al., supra. Extraction with demineralisation was carried out using EDTA (10%). The manner in which the bone material was comminuted was not published.

For bSGF it is mentioned that an EDTA extract was obtained from bovine bone, but the bone was not specifically defined; Jennings et al., supra. There are no details concerning the manner in which the bone material was comminuted. bBMP was obtained from tubular bone. The bones, cooled in liquid nitrogen, were ground to meal in a Whiley mill, freed from fat and washed. The meal was subsequently demineralised with 0.6M HCl; see Urist et al., supra. CIF-A and CIF-B were obtained from metatarsal bovine bone. The bones were pulverised in a mill cooled by liquid nitrogen In this case demineralisation was with 0.5M HCl. Extraction was carried out with 4M guanidinium hydrochloride/10 mM EDTA; see Seyedin et al., supra. BDGF-2 does not have to be extracted since this factor is released by embryonic tissue into the surrounding culture medium; see Canalis et al., supra.

rSGF was extracted from not specifically defined tubular bones of rats using a mixture of 4M guanidinium hydrochloride/EDTA (10%); see Sibonga et al. (1985) Proc. Fed. Am. Soc. Exp. Biol. 44, p. 1099, No. 4028.

Concentration

There is no data in the literature for hSGF relating to binding to hydroxyapatite.

There is no data in the literature concerning binding to hydroxyapatite for CIF-A, CIF-B and BDGF-2. bBMP binds to hydroxyapatite but has not been tested either in organ culture or in monolayer cultures bSGF can be concentrated by binding to hydroxyapatite. The process described consists of two steps:
1) binding to hydroxyapatite, elution with phosphate buffer;

2) binding to hydroxyapatite, elution with phosphate buffer in the presence of 4M guanidinium hydrochloride.

For the total mitogenic activity according to these two steps, a concentration factor of approximately 14 for a total yield of mitogenic activity is indicated, but this cannot be clearly calculated from the data in the literature; see Jennings et al., supra.

rSGF binds to hydroxyapatite, but no exact conditions have been given; see Sibonga et al., supra.

Growth-promoting factors of bone material from pigs are not so far known.

Another object of the invention is to provide a growth-stimulating material that is particularly suitable for the therapeutic composition of the invention.

This object is achieved by a growth-stimulating material consisting of or comprising one or more growth-promoting (mitogenic) factors that can be obtained by the invention the steps of claim 8 and optionally, in addition, the steps of claim 9 and optionally claim 10, and that is characterised by the features of the characterising clause of claim 2.

The invention also relates to a process for obtaining growth-stimulating material.

DESCRIPTION OF THE PREFERRED EMBODIMENTS OF THE INVENTION

Microtitre plate test system

The growth-stimulating material according to the invention is tested in microtitre plates in an optimised test system automated as regards the cell harvest. This test system provides the following steps:

(a) The incorporation of $^3$H-labelled thymidine into the total DNA of osteoblast precursor cells is carried out by plating out these osteoblast precursor cells onto microtitre plates, without change of media, in a concentration of foetal calf's serum (FCS) that is less than 0.5% (calculated by volume).

(b) The cell density of osteoblast precursor cells, which respond to the addition of the growth-stimulating material of the invention having the actions and properties the invention by an increase in the incorporation of $^3$H-thymidine into the total DNA, is in the range of from 2,500 to 15,000 cells per microtitre well (6 mm diameter) at the time of plating out.

(c) The maximum response (incorporation of $^3$H-thymidine into the total DNA after the addition of the growth-stimulating material of the invention having the actions and properties of the invention is recorded at a cell density of 5,000 osteoblast precursor cells per microtitre well (6 mm diameter) at the time of plating out and after growth of these osteoblast precursor cells for 4 days and with an incubation of from 16 to 22 hours.

(d) The incorporation of $^3$H-thymidine into the total DNA after the addition of the growth-stimulating material according to the invention having the actions and properties according to the invention is, in the case of chondrocytes in microtitre plates (6 mm diameter per microtitre well) at an FCS concentration of less than 0.5% (calculated by volume), at a cell concentration of from 1,250 to 10,000 chondrocytes per microtitre well at the time of plating out, increased on the first, second and third day after plating out.

(e) The incorporation of $^3$H-thymidine into the total DNA of adherent cell cultures in microtitre wells is achieved by the following method. The adherent cell cultures are lysed in the microtitre wells after removal of the radioactive medium and after the washing operations. Subsequently, the total DNA is precipitated in the microtitre wells by acid. The precipitated total DNA and the radioactivity ($^3$H-thymidine) contained in it are transferred simultaneously from several mircotitre wells onto filter paper using an automatic cell-harvesting device The rate of incorporation is then determined.

In the following the invention is explained in detail by way of Examples..

EXAMPLE 1

50 kg of bone material from pigs was freed from skin, flesh and fat at +4° C., cooled in liquid $N_2$ and stored at −20° C. The bone material was compressed with a compressing device while cooling with liquid $N_2$, resulting in a total yield of 10 kg of bone meal of a particle size of from 0.5 to 2 mm.

1 kg of bone meal was dialysed for 2 weeks in dialysis tubes against 10% EDTA (weight/volume), and the dialysis solution was changed twice. Then, the supernatant solution in the dialysis tubes was homogenised with the insoluble residue in a Star mix. The suspension was centrifuged twice, in each case the pellet was discarded, and the supernatant was heated at 75° C. for 15 minutes. The precipitated protein was removed by centrifugation and the supernatant was brought to a pH of 3.0 with 1N HCl for 20 minutes. The precipitated protein was again removed by centrifugation and the supernatant was brought to a pH of 7.2 with 1N NaOH. Dialysis was then carried out against 25 mM phosphate buffer, pH 7.2. 780 ml of crude extract having a protein content of 218 μg/ml=170 mg total protein were obtained. This crude extract was applied to a hydroxyapatite column having a diameter of 5 cm and a height of 30 cm and washed with 25 mM phosphate buffer (2 L) and with 380 ml of a phosphate gradient increasing from 25 mM to 100 mM. Elution was then carried out with 4M guanidinium HCl. The active fractions from the elution with 4M guanidinium.HCl were pooled, dialysed against 4M guanidinium.HCl and applied to a gel filtration column, with 4M guanidinium.HCl as eluant, which column had previously been calibrated with standard proteins. The active fractions in a molecular weight range of 24±8 kD were eluted from this gel fitration column. The active fractions of the hydroxyapatite column and the gel filtration column were dialysed against 25 mM phosphate buffer. The dose-dependent increase in the incorporation of $^3$H-thymidine into DNA of osteoblast precursor cells was determined for the products of the individual purification steps. One unit was defined as the protein concentration at which the semi-maximum stimulation of these cells in the incorporation of $^3$H-thymidine occurs. The following values were obtained:

| | specific activity (units/μg) | total units | total protein (μg) | concentration |
|---|---|---|---|---|
| crude extract | 13 | 2,210,000 | 170,000 | 1 |
| hydroxyapatite | 500 | 1,547,000 | 3,094 | 38 |
| gel filtration | 3,300 | 330,000 | 100 | 254 |

EXAMPLES 2 AND 3 AND COMPARISON EXAMPLES 1 AND 2

In an animal experiment carried out on a narcoticised dog, the bone in the lower jaw region was exposed by preparation of a mucoperiosteal flap. Then, boreholes (diameter 2.8 mm, depth 5 mm) were made with a standard internally cooled implant drill. These holes were filled with a preparation of hydroxyapatite, with growth-stimulating material according to Example 1 or with sodium chloride, in the amounts indicated:

| | Preparation | | |
|---|---|---|---|
| | HAP (parts by wt.) | Growth-stimulating material (parts by vol.) | NaCl (parts by wt.) |
| Example | | | |
| 2 | $250 \times 10^3$ | 50 | 0 |
| 3 | $250 \times 10^3$ | 50 | 0 |
| Comparison Example | | | |
| 1 | $250 \times 10^3$ | 0 | 50 |
| 2 | 0 | 0 | 0 Hole remained exposed |

After eight weeks the hole in each of Examples 2 and 3 and Comparison Example 2 was completely sealed, whilst in Comparison Example 1, in the upper region only osseous regeneration with the exception of the central third had taken place. It can be concluded from this that the growth-stimulating material in Examples 2 and 3 caused an improvement in the new bone formation as compared with Comparison Example 1.

EXAMPLES 4 AND 5 AND COMPARISON EXAMPLES 3 AND 4

Examples 2 and 3 and Comparison Examples 1 and 2 were repeated and the evaluation was carried out after 3 weeks.

In Example 4 the hole exhibited in the upper region and basally, as far as half way, a spongy lamellar new bone formation (with integration of the peripheral preparation particles).

In Example 5 there was a lamellar new bone formation with integration of the preparation particles in the outer third to half of the upper region of the hole, and basally the entire hole was almost completely filled by trabeculae with integration of the preparation particles.

In Comparison Example 3, it was possible to observe new bone formation in the upper region of the hole in the outer third of half of the circumference without incorporation of the preparation particles; basally there was new bone formation in the outer half with partial incorporation of the preparation particles which were fibrously centrally separated.

In Comparison Example 4, newly formed trabeculae filled the hole of one specimen almost completely and the hole of another specimen up to the central third.

We claim:

1. A composition which comprises:
I an active ingredient prepared by
   (a) cooling in liquid nitrogen fat-free bone material of metacarpalia from pigs;
   (b) comminuting the bone material at the temperature of liquid nitrogen, to bone meal of a particle size in the range from 0.5 to 2 mm;
   (c) demineralizing the bone particles in an aqueous solution; and
   separating from the resulting solution, the active ingredient having the following features:
   (a) the active ingredient causes a dose-dependent growth stimulation of fibroblasts, osteoblast precursor cells and chondrocytes and embryonic tissue of chickens in monolayer cell cultures;
   (b) the active ingredient causes a dose-dependent growth of embryonic tubular bones of chickens in organ culture in vitro, due to a proliferation of chondrocytes in the growth zone;
   (c) the active ingredient does not cause any increased incorporation of $^3$H-thymidine into DNA of calvaria cells in the microtitre plate test system;
   (d) the feature (a) or (b) above are retained for at least 15 minutes at a temperature of from 55° to 75° C.;
   (e) the features (a) or (b) above are retained for at least 20 minutes at a pH of approximately 3 and of approximately 10;
   (f) the active ingredient can be eluted on a gel filtration column under high salt conditions in a molecular weight range of $24 \pm 8$ kD;
   (g) the active ingredient runs through a copper sulphate-chelate column without being adsorbed, it being possible for the specific activity to be concentrated by a factor of from 5 to 20;
   (h) the active ingredient can be bound to a reversed phase column in high pressure liquid chromatography and eluted with an acetonitrile/water mixture having an acetonitrile content in the range of from 10 to 45% calculated by volume;
   (i) 100 to 200 pg of the active ingredient forms more than 5 mm$^3$ bone mass growth; and
   (ii) the active ingredient can be dialysed against 25 mM phosphate buffer; and
II a solid carrier to bind the active ingredient to the site of application.

2. A composition according to claim 1 wherein the carrier is a partially to fully absorbable carrier.

3. A composition according to claim 1 having a ratio of active ingredient material:solid carrier of 1:1000 to 1:200,000 (volume:weight).

4. A process for obtaining the active ingredient according to claim 1, which comprises;
cooling in liquid nitrogen fat-free bone material of metacarpalia from pigs;
comminuting the bone material to bone meal of a particle size in the range of from 0.5 to 2 mm at the temperature of liquid nitrogen;
demineralizing the bone meal particles with an aqueous solution;
dialysing the resulting aqueous suspension to extract the active ingredient;
acidifying the supernatent to an acid pH;
heating the acidified supernatent to a temperature sufficient to precipitate protein; and
centrifuging off insoluble components.

5. The process according to claim 4, wherein, the aqueous supernatant obtained after centrifugation is applied to a chromatography column of hydroxyapatite and eluted with guanidinium hydrochloride.

6. The composition of claim 1 wherein the solid carrier is selected from the group consisting of hydroxyapatite, tricalcium phosphate, and collagen.

7. The composition of claim 1 wherein separation of the active ingredient comprises dialysis, acidification of the dialysis supernatent, heating of the supernatent and centrifugation to remove insolubles.

8. The composition of claim 7 wherein the separated active ingredient is applied to a hydroxyapatite column and eluted with guanidinium hydrochloride.

9. The composition of claim 8 wherein the eluate is applied to a gel filtration column and eluted under high salt conditions in a molecular weight range of approximately 24±8 kD.

10. A composition useful as a mitogenic factor, which is prepared by;
  (a) cooling in liquid nitrogen fat-free bone material of metacrapalia from pigs;
  (b) comminuting the bone material at the temperature of liquid nitrogen, to bone meal of a particle size in the range from 0.5 to 2 mm;
  (c) demineralizing the bone particles in an aqueous solution;
  (d) dialyzing the aqueous solution against a 10 percent (weight/volume) solution of N,N,N',N',-ethylenediaminetetraacetic acid;
  (e) heating the supernatent at a temperature of 75° C. for 15 minutes to precipitate protein; and
  (f) acidifying the solution to a pH of 3.0; and
  (g) centrifuging to remove precipitated protein; said composition having the following features:
    (a) a dose-dependent growth stimulation of fibroblasts, osteoblast precursor cells and chondrocytes and embryonic tissue of chickens in monolayer cell cultures;
    (b) a dose-dependent growth of embryonic tubular bones of chickens in organ culture in vitro, due to a proliferation of chondrocytes in the growth zone;
    (c) do not cause any increased incorporation of $^3$H-thymidine into DNA of calvaria cells in the microtitre plate test system;
    (d) the feature (a) and (b) above are retained for at least 15 minutes at a temperature of from 55° to 75° C.;
    (e) the features (a) or (b) above are retained for at least 20 minutes as a pH of approximately 3 and of approximately 10;
    (f) the composition can be eluted on a gel filtration column under high salt conditions in a molecular weight range of 24±8 kD;
    (g) the composition run through a copper (11) sulphate-chelate column without being adsorbed, it being possible for the specific activity to be concentrated by a factor of from 5 to 20;
    (h) the composition can be bound to a reversed phase column in high pressure liquid chromatography and eluted with an acetonitrile/water mixture having an acetonitrile content in the range of from 10 to 45%;
    (i) 100 to 200 μg of the active ingredient forms more than 5 mm$^3$ bone mass growth; and
    (j) the active ingredient can be dialysed against 25 mM phosphate buffer; and
  II a solid carrier to bind the active ingredient to the site of application.

11. The composition of claim 10 wherein after centrifuging, the supernatent is applied to a chromatography column of hydroxyapatite and eluted with guanidinium hydrochloride and the eluate is applied to a gel filtration column and eluted with 4M guanidinium hydrochloride in a molecular weight range of approximately 24±8 kD.

* * * * *